(12) United States Patent
Houjou et al.

(10) Patent No.: US 11,209,721 B2
(45) Date of Patent: Dec. 28, 2021

(54) IMAGING DEVICE AND OPTICAL UNIT

(71) Applicant: CASIO COMPUTER CO., LTD., Tokyo (JP)

(72) Inventors: Yoshiharu Houjou, Tokyo (JP); Jumpei Ishibashi, Nishitokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 16/119,759

(22) Filed: Aug. 31, 2018

(65) Prior Publication Data
US 2019/0094662 A1 Mar. 28, 2019

(30) Foreign Application Priority Data
Sep. 27, 2017 (JP) .............................. JP2017-186797

(51) Int. Cl.
| | | |
|---|---|---|
| *G03B 17/55* | (2021.01) | |
| *G03B 15/03* | (2021.01) | |
| *A61B 1/12* | (2006.01) | |
| *A61B 1/24* | (2006.01) | |
| *G03B 17/08* | (2021.01) | |
| *A61B 1/06* | (2006.01) | |

(52) U.S. Cl.
CPC ............ *G03B 17/55* (2013.01); *A61B 1/0607* (2013.01); *A61B 1/0676* (2013.01); *A61B 1/0684* (2013.01); *A61B 1/128* (2013.01); *A61B 1/24* (2013.01); *G03B 15/03* (2013.01); *G03B 17/08* (2013.01)

(58) Field of Classification Search
CPC ........ G03B 17/55; G03B 17/08; G03B 15/03; A61B 1/128; A61B 1/24; A61B 15/03; F21K 9/232; F21V 29/76; F21V 29/763; F21V 29/773
See application file for complete search history.

(56) References Cited

U.S. PATENT DOCUMENTS

| | | | |
|---|---|---|---|
| 6,171,105 B1* | 1/2001 | Sarmadi ............... | A61C 19/004 433/29 |
| 8,269,828 B2* | 9/2012 | Miller .................. | H04N 5/2256 348/80 |
| 2005/0116179 A1* | 6/2005 | Aguirre ................ | A61C 19/004 250/492.1 |
| 2009/0076321 A1 | 3/2009 | Suyama et al. | |

(Continued)

FOREIGN PATENT DOCUMENTS

| | | |
|---|---|---|
| CN | 101272726 | 9/2008 |
| JP | 2007167547 A | 7/2007 |
| JP | 2009261830 A | 11/2009 |

OTHER PUBLICATIONS

Chinese Office Action (and English translation thereof) dated Jul. 22, 2020, issued in Chinese Application No. 201811132625.8.

(Continued)

*Primary Examiner* — Heidi M Eide
*Assistant Examiner* — Drew S Folgmann
(74) *Attorney, Agent, or Firm* — Holtz, Holtz & Volek PC

(57) ABSTRACT

An imaging device having an imaging lens system includes: an outermost cover member of the imaging lens system; a light source arranged inside the cover member; and a heat dissipation member is configured to dissipate heat of the light source to the cover member, thereby defogging the cover member by heat of the heat dissipation member.

10 Claims, 7 Drawing Sheets

(56) References Cited

U.S. PATENT DOCUMENTS

| | | | |
|---|---|---|---|
| 2009/0208894 A1* | 8/2009 | Orloff | A61C 19/004 433/29 |
| 2014/0104479 A1* | 4/2014 | Samuels | G03B 17/55 348/335 |
| 2014/0168507 A1* | 6/2014 | Renaud | G03B 17/55 348/373 |
| 2017/0172403 A1* | 6/2017 | Fink | A61B 1/24 |
| 2017/0302874 A1* | 10/2017 | Adair | G06F 1/1686 |
| 2018/0013272 A1* | 1/2018 | Germe | H02G 3/04 |
| 2018/0140196 A1* | 5/2018 | Khosravi Simchi | A61B 5/0077 |

OTHER PUBLICATIONS

Chinese Office Action (and English translation thereof) dated Jan. 25, 2021 issued in Chinese Application No. 201811132625.8.

\* cited by examiner

IMAGING DEVICE AND OPTICAL UNIT

BACKGROUND

1. Technical Field

The present invention relates to an imaging device, particularly, an imaging device to photograph a highly moist place.

2. Related Art

In recent years, owing to miniaturization of a digital camera and progress in photographing attachments to a smartphone, a dentist and an oral surgeon have more opportunities to take photographs of a patient's oral cavity in order to diagnose the same, and due to such situations, a camera for intraoral photographing is developed (JP 2007-167547 A, for example).

JP 2007-167547 A discloses a digital camera for intraoral photographing that has no hygienic problem, allows a dentist to easily monitor a target inside a patient's oral cavity on a screen at the time of using the camera, and also allows the patient to easily see the same on the screen. The digital camera for intraoral photographing includes: a camera body formed of a lens barrel portion to be inserted into the oral cavity, an intermediate portion formed continuous with the lens barrel portion, and a grip portion formed continuous with the intermediate portion; and a dental appliance detachably fitted to the lens barrel portion, in which a liquid crystal display device is mounted on the intermediate portion of the camera body.

This digital camera for intraoral photographing has a built-in rechargeable battery and is accompanied by functions to supply DC electricity to the battery and simultaneously preheat the dental appliance when the camera is not in use. The functions are provided in order to charge the battery by a battery charger when the camera is not in use, and also to heat a mirror for intraoral observation to prevent fogging at the mirror when the mirror is inserted into a patient's oral cavity by transmitting heat of electric components that have consumed DC electricity to the mirror via a metallic outer cylinder provided in the dental appliance.

SUMMARY

A mode of the present invention is an imaging device that includes an imaging lens system and is characterized in including: an outermost cover member of the imaging lens system; a light source arranged on an inner side of the cover member; and a heat dissipation member configured to dissipate heat of the light source to the cover member.

Other characteristics of the present invention will be clarified by the description of the present specification and the accompanying drawings.

BRIEF DESCRIPTION OF THE DRAWINGS

FIG. 5A is a plan view, FIG. 5B is a bottom view, FIG. 5C is a side view taken along an arrow II-II in FIG. 5A, and FIG. 5D is a side view taken along an arrow in FIG. 5A;

DETAILED DESCRIPTION

In the following, an embodiment of a camera to which the present invention is applied will be described with reference to the drawings. Note that the camera is mainly applied in a case of photographing the inside of a body cavity such as an oral cavity, but in the description of the specification of the present application, a case of photographing the oral cavity will be describe as a representative thereof.

Entire Structure of Camera 1

A camera 1 according to the present embodiment prevents a cover member from being fogged at the time of inserting a distal end portion of a camera lens into an oral cavity having a temperature (36 to 37 degrees) higher than an examination room temperature, by heating a space of the lens distal end portion by utilizing heat dissipation of an LED provided to brightly illuminate an imaging region in the oral cavity. The more detail description will be provided below.

Figure 1:
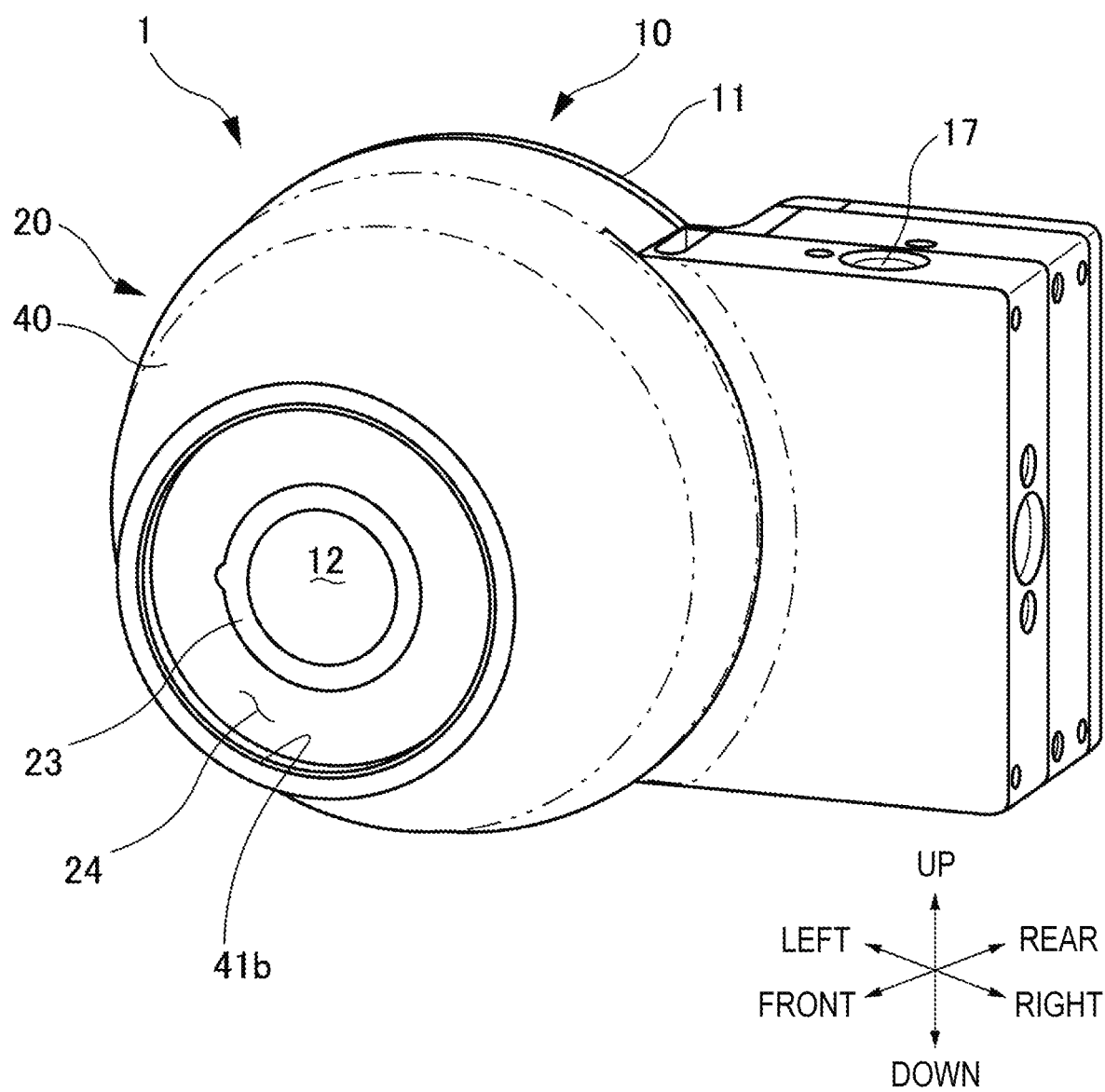
FIG. 1 is a perspective view of an imaging device according to the present embodiment.
Figure 2:
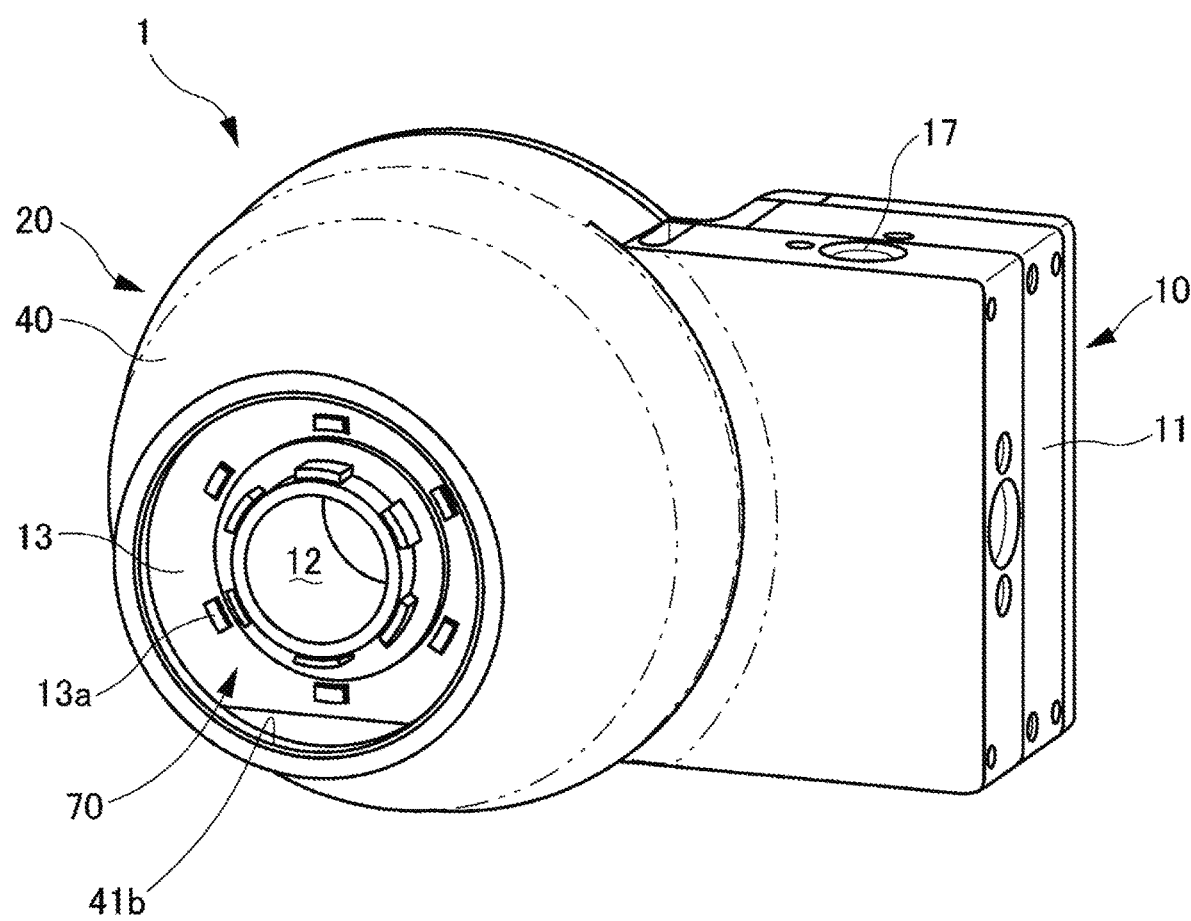
FIG. 2 is an explanatory view in which a cover member of a lens unit in FIG. 1 is detached.
Figure 3:
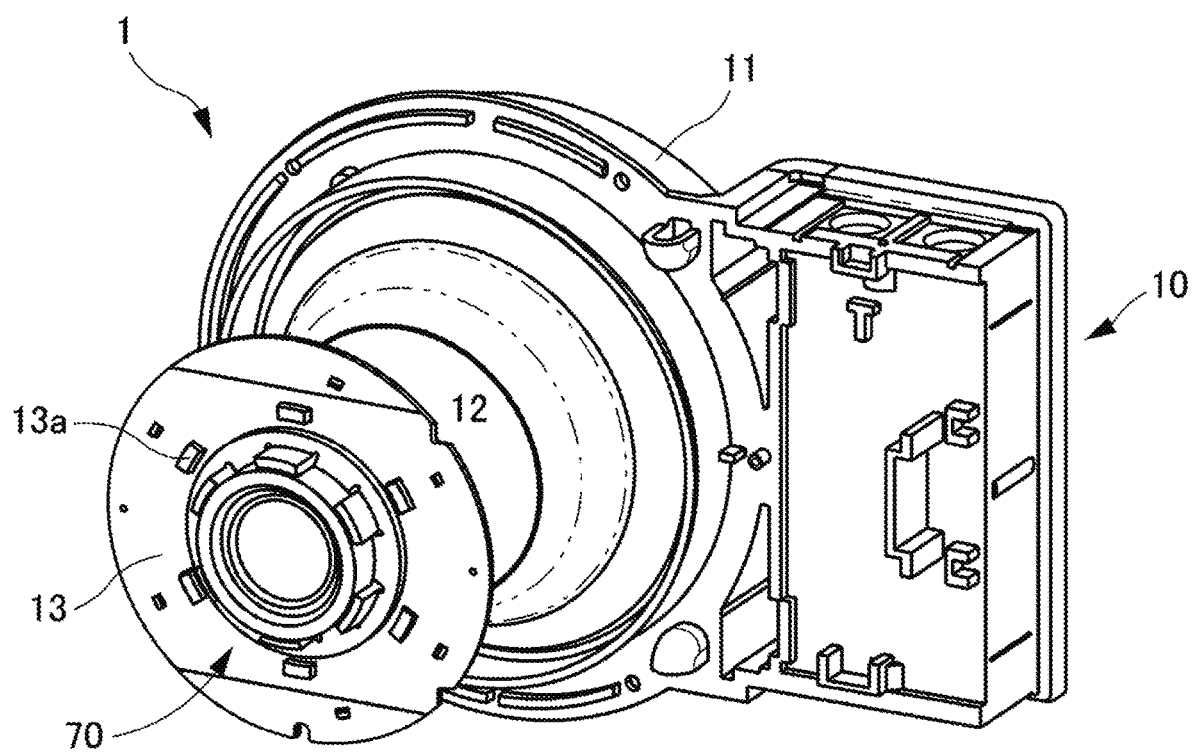
FIG. 3 is an explanatory view in which a cover body of the lens unit in FIG. 2 is detached.
Figure 4:
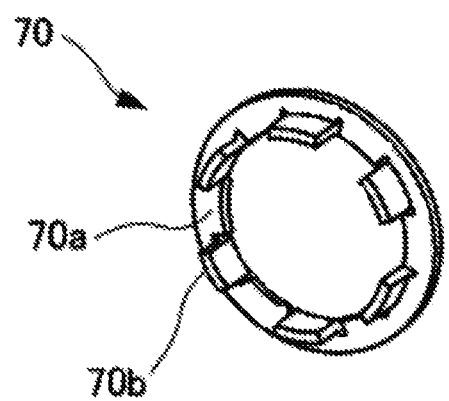
FIG. 4 is a perspective view of a heatsink provided in the imaging device according to the present embodiment.
Figure 5A:
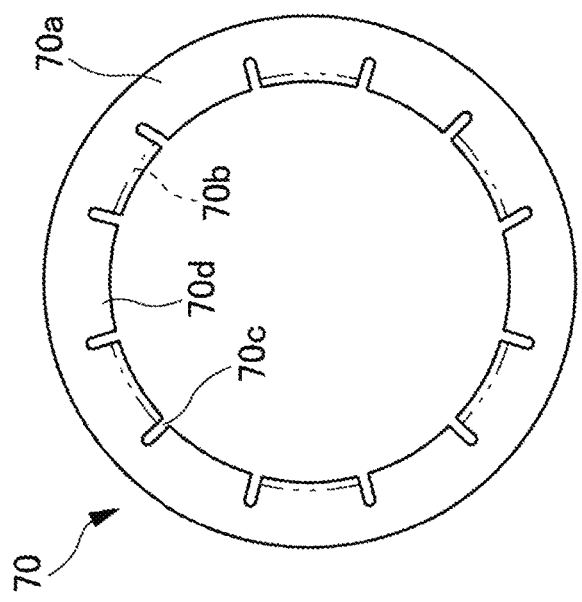
FIGS. 5A to 5D are explanatory enlarged views of the heatsink in FIG. 4.
Figure 5B:
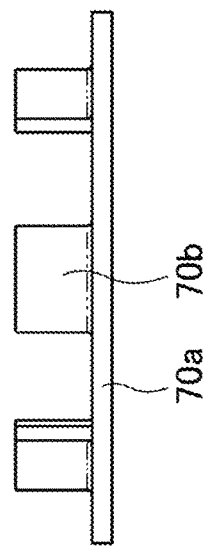
Figure 5C:
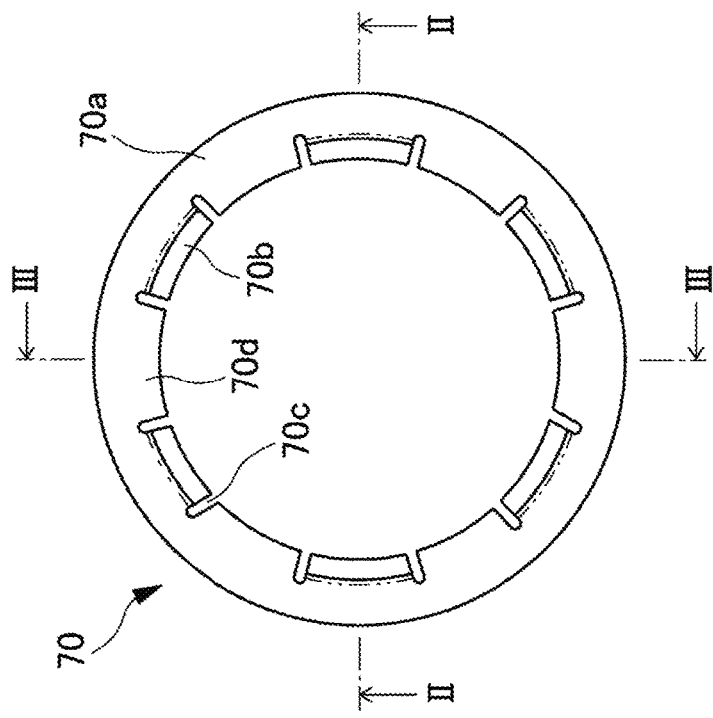
Figure 5D:
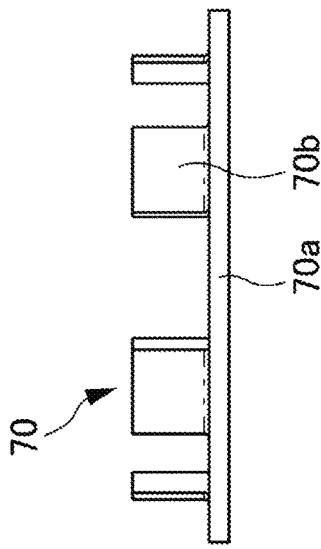
Figure 6:
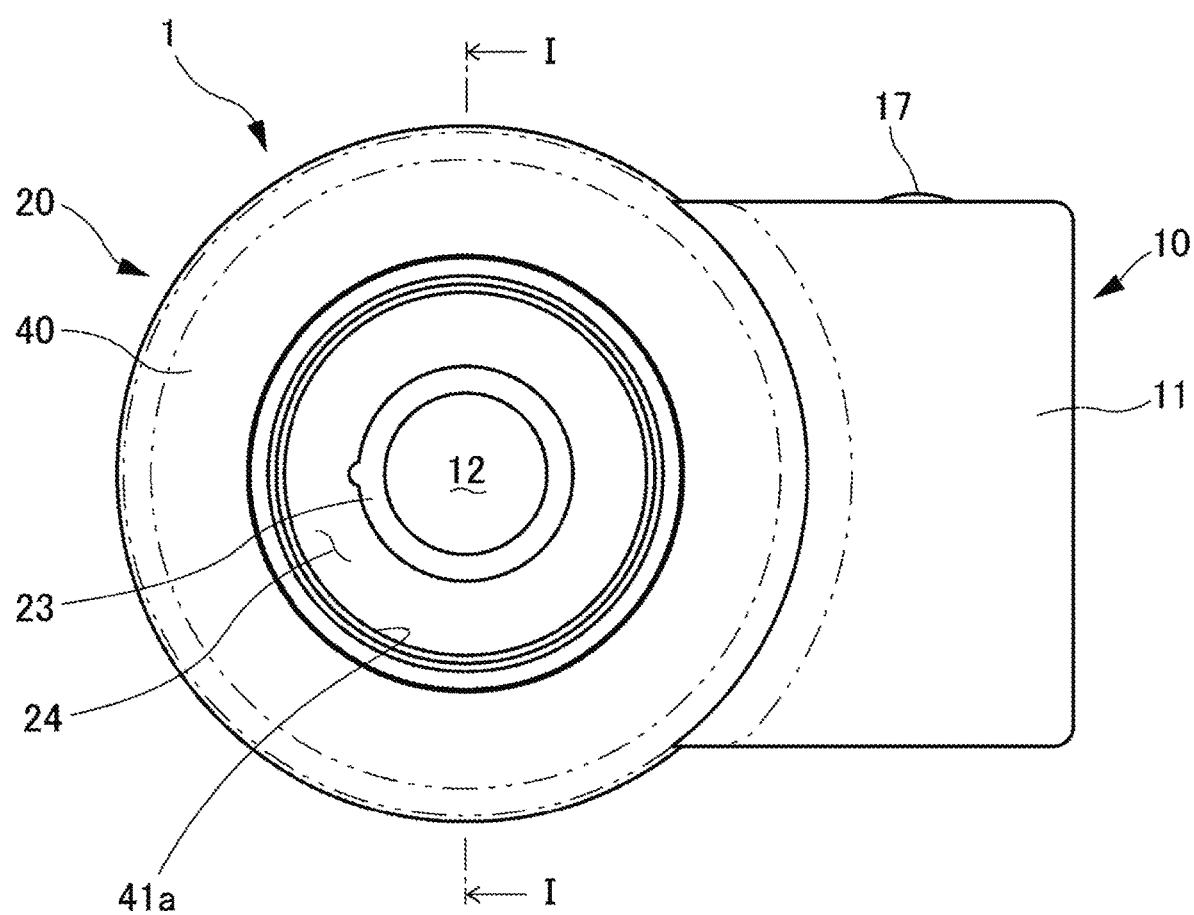
FIG. 6 is a front view of the imaging device according to the present embodiment.
Figure 7:
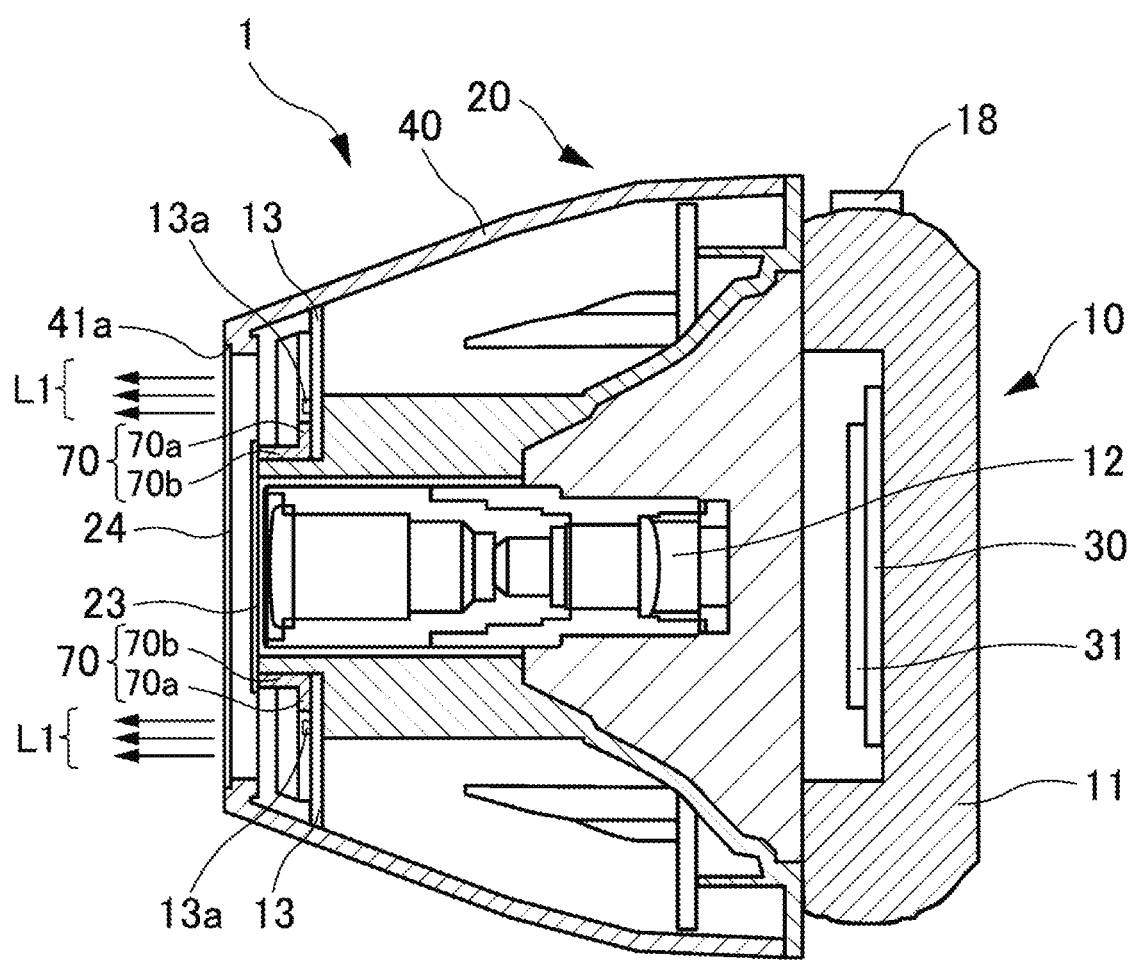
FIG. 7 is a cross-sectional view of the imaging device taken along a cutting plane line I-I in FIG. 6.

FIG. 1 is a perspective view of the imaging device according to the present embodiment. FIG. 2 is an explanatory view in which the cover member of a lens unit in FIG. 1 is detached. FIG. 3 is an explanatory view in which a cover body of the lens unit in FIG. 2 is detached. FIG. 4 is a perspective view of the heatsink provided in the imaging device according to the present embodiment. FIGS. 5A to 5D are explanatory enlarged views of the heatsink in FIG. 4, FIG. 5A is a plan view, FIG. 5B is a bottom view, FIG. 5C is a side view taken along an arrow II-II in FIG. 5A, and FIG. 5D is a side view taken along an arrow III-III in FIG. 5A. FIG. 6 is a front view of the imaging device according to the present embodiment. FIG. 7 is a cross-sectional view of the imaging device taken along a cutting plane line I-I in FIG. 6.

As illustrated in FIGS. 1 to 7, a camera (imaging device) 1 is substantially formed of a camera body (referred to as an imaging device body and also simply referred to as "main body") 10 and a lens unit 20 provided in front of the camera body 10. The lens unit 20 is inserted into a body cavity such as an oral cavity to a predetermined extent, and photographs a subject. In the case of the oral cavity, an entire region in the oral cavity is photographed as the subject in order to confirm presence of oral cancer (tongue cancer, gingival cancer, mouth bottom cancer, buccal mucosal cancer, and the like) or presence of a tumor thereof.

Note that, in the following description, the description will be provided on the basis of an orthogonal coordinate system, as illustrated in FIG. 1, by setting: an imaging target side as the front side (front surface or front face) of the camera 1; an opposite side thereof as a rear side; and vertical and horizontal directions at the time of viewing the camera 1 from the front side as the vertical and horizontal directions as they are. Additionally, as for installation of each of the members, an appropriate method such as installation using a screw or a small screw, or installation using fitting or the like may be adopted unless otherwise particularly specified.

Structure of Camera Body 10

As illustrated in FIGS. 1 and 2, the camera body 10 includes a housing 11, and the housing 11 includes, inside thereof: an imaging lens system (e.g., zoom lens) 12; and a light emitting diode (LED) substrate 13 on which a plurality of LEDs 13a serving as light sources is mounted. Additionally, as illustrated in FIG. 6 described later, the camera body 10 houses various kinds of components such as a circuit wiring board 30 and an imaging element 31 on the rear side of the imaging lens system 12. The housing 11 has an upper surface provided with a shutter button 18 (see FIG. 7) and a power button 17.

Additionally, the inside of the housing 11 is provided with: a storage unit to store a photographed image read by the imaging element 31 in response to operation of the shutter button 18; a control unit to control each of the above-described components; and a battery unit to supply power to the above-described respective components, but illustrations thereof are omitted.

In the camera body 10, a known photographing device used for normal photographing, such as a structure of a commercially available digital camera, can be adopted and, known components can be used as the imaging lens system 12, circuit wiring board 30, and imaging element 31, for example. The imaging lens system 12 includes a known optical lens. Additionally, as the imaging element 31, a charge coupled device (CCD) image sensor or a complementary metal oxide semiconductor (CMOS) image sensor can be used. Furthermore, the camera body 10 is provided with a touch panel screen (not illustrated) in order to display a captured image and execute various kinds of settings for the camera 1.

Structure of Lens Unit 20

As illustrated in FIGS. 1 to 3, the lens unit 20 includes: a cylindrical cover body 40 having a shape obtained by cutting a top of a truncated cone (the cover body 40 is detached in FIG. 3); a cover member 24 fitted into an opening 41b of the cover body 40; and a filter 23 surrounding a forefront of the imaging lens system 12.

The cover body 40 is made of a resin such as a polyvinyl chloride derivative or an acrylic resin. An outer shape of the cover body 40 has a shape that is tapered toward the front side, and the inside thereof is hollow. Additionally, the hollow portion of the cover body 40 also has a shape having a diameter gradually decreased toward the front side.

As illustrated in FIG. 2, the LED substrate 13 on which the LEDs 13a are mounted is provided on the rear side of the cover member 24 of the cover body 40 in a manner surrounding the imaging lens system 12. The LED substrate 13 has an annular shape, and a plurality of LEDs 13a (for example, six) is mounted on the front surface thereof. As illustrated in FIGS. 2 and 3, the six LEDs 13a are arranged at equal intervals on a concentric circle with respect to a center of the LED substrate 13. With this structure, the LED substrate 13 on which the LEDs 13a are mounted functions as a ring flash that emits light forward from an outer circumferential position of the imaging lens system 12. Each of the LEDs 13a is formed of an LED that emits white light.

The LEDs 13a are arranged on a distal end portion of the cover body 40 of the lens unit 20 in order to illuminate the inside of the oral cavity at the time of magnifying and photographing teeth, gums, a tongue, a buccal mucosa, and the like in the oral cavity.

The cover member 24 is fitted into the opening 41b formed at the distal end of the cover body 40 and is closely arranged on the front side of the LEDs 13a. The cover member 24 is made of a synthetic resin such as transparent glass or acrylic, and transmits light emitted from the filter 23 toward the front side. During photographing, the cover member 24 is in a state of being set close to or inserted into the oral cavity, but since the camera 1 also performs sterilization, cleaning, and the like after intraoral photographing, the cover member 24 and the cover body 40 are surely sealed. With such sealing, the lens is waterproofed such that saliva, water droplets from fogs, and the like in the oral cavity do not adhere directly to the lens, and also a temperature of a sealed space inside the cover member 24 is increased.

Here, as illustrated in FIGS. 2 and 3, a heatsink 70 is mounted on the LED substrate 13. The heatsink 70 dissipates heat generated from the LEDs 13a and is made of a metal such as aluminum or copper having good heat transfer characteristics. The heatsink 70 has a shape to dissipate heat toward the cover member 24, and an example thereof is illustrated in FIG. 4. As illustrated in FIG. 4, the heatsink 70 has an annular seat portion 70a and protruding portions 70b each extending from the seat portion 70a.

The heatsink 70 will be described with reference to the enlarged view of FIGS. 5A to 5D. As illustrated in FIGS. 5A and 5B, edge pieces 70d respectively partitioned by a plurality of cut-way portions 70c are formed on an inner peripheral edge of the annular seat portion 70a, and each of the protruding portions 70b is erected in each of the edge pieces 70d located at positions corresponding to each of the LEDs 13a. Here, illustrated is an example in which the six protruding portions 70b are provided in a manner corresponding to the six LEDs 13a, but the number of the protruding portions 70b may be arbitrarily set considering the number of arranged LEDs 13a, or the like.

Additionally, each protruding portion 70b is formed in an arcuate plate shape (see FIGS. 5A and 5B), but the shape of the protruding portion 70b is not limited to this type and may have another type. For example, the shape may be a stick type like a pin holder, or may be a waveform-like plate type. In short, each protruding portion may be formed so as to transmit heat generated from each LED 13a and increase the temperature inside the cover member 24. Meanwhile, since each LED 13a may shorten a lifetime of the LED itself in a case of not efficiently dissipating heat, the heatsink 70 functions from such a viewpoint as well.

By the way, in the present embodiment, illustrated is a non-contact mode in which the heatsink 70 does not directly contact the cover member 24 (see FIG. 7). In other words, the protruding portions 70b of the heatsink 70 contact the filter 23. With this structure, the filter 23 is heated by the protruding portions 70b, and the temperature in a space between the filter 23 and the cover member 24 is increased. As for whether to perform indirect heating by setting the heatsink 70 not to contact the cover member 24 or perform direct heating by setting the heatsink 70 to contact the cover member 24, any of the modes may be adopted considering a material of the cover member 24 and a required level of fog prevention, a heat generation amount of each LED 13a, and the like.

Travel Course of LED Light During Intraoral Photographing

FIG. 7 is a cross-sectional view of the camera 1 illustrated in FIG. 6 during intraoral photographing. Light emitted from each LED 13a passes through the cover member 24 and is linearly emitted forward as indicated by an arrow L1. The LEDs 13a emitting such light are arranged at equal intervals on the circumference provided outside the imaging lens system 12, and are arranged on a plane substantially same as the imaging lens system 12.

Exemplary Use of Camera 1

In a case of performing intraoral photographing by using the camera 1, a photographer attaches the lens unit 20 to the camera body 10 as illustrated in FIG. 1. At this point, as for a mode to attach the lens unit 20 to the camera body 10, a known structure can be adopted. For example, the lens unit 20 may be screwed into the camera body 10 or magnetically attracted thereto by using a magnetic material. Additionally, the lens unit 20 may be attached to the camera body 10 in a rotatable manner by providing a rotational portion (not illustrated) in the lens unit 20 and providing a rotation support portion in the camera body 10, respectively.

Then, the photographer sets the lens unit 20 close to or partly inserts the lens unit 20 into the oral cavity, turns on power by pressing the power button 17 to brightly illuminate the oral cavity by emitting light from the LEDs 13a by pressing, for example, the shutter button 18 halfway. An intraoral lesion site is magnified 10 to 30 times via the imaging lens system 12, and an image is formed on the imaging element 31 of the camera body 10. When the shutter button 18 of the camera body 10 is fully pressed at arbitrary timing, a captured image read by the imaging element 31 is stored in the storage unit of the camera body 10. The captured image thus stored can be used for examination and diagnosis.

Effects of Embodiment

As described above, in the camera 1 according to the present embodiment, it is possible to provide the camera 1 by which: a brightly-illuminated oral cavity can be photographed in a state where the front surface of the camera body 10 is covered with the lens unit 20; and the distal end of the lens unit 20 can be surely prevented from being fogged during photographing.

More specifically, as the camera 1 to photograph the oral cavity, it is necessary to brightly illuminate the oral cavity with a large number of LEDs 13a, but in the present embodiment, a dark oral cavity can be stably illuminated by arranging the plurality of LEDs 13a at the distal end portion of the lens unit 20 on the circumference of the center axis of the lens.

Additionally, the oral cavity generally has the temperature (36 to 37 degrees) higher than a normal room temperature and an examination room temperature, and fogging tends to occur when the distal end portion of the lens unit 20 is inserted into the oral cavity. In contrast, according to the present embodiment, fogging can be prevented during intraoral photographing by: dissipating, to the cover member 24, heat of the LEDs 13a that illuminate light; and simultaneously heating the space inside the cover member 24.

Thus, since it is possible to surely prevent the lens unit 20 from being fogged during intraoral photographing, a clear image can be stored in the storage unit, a diagnosis time can shortened by reducing necessity to redo photographing, and also accurate diagnosis can be performed.

Furthermore, since there is no need to prepare another heat source to prevent fogging, it is possible to provide the camera 1 for intraoral photographing in which both of illumination and fogging prevention can be performed by a simple and inexpensive structure.

Modification of Embodiment

The present embodiment is not limited to the embodiment described above, and various modifications and applications can be made. In the above-described embodiment, described is the case where the lens unit 20 can be rotatably attached to the camera body 10, but a movement mode of the lens unit 20 is not limited to rotation and may also be a mode in which the lens unit is slidable with respect to the camera body 10. In short, the lens unit 20 is at least arranged in a manner covering the front side of the imaging lens system 12 during intraoral photographing. Note that the imaging lens system 12 may be structured as a fixed focus lens instead of a zoom lens, considering use of the camera 1 and the like.

Additionally, in the above-described embodiment, described is the case where the LEDs 13a arranged on the circumference are used as the light source in the present invention, but another light source may also be adopted. For example, a high luminance light such as a halogen lamp, a semiconductor light emitting element, and a light emitting element such as organic electroluminescence can also be used.

Additionally, described is the case where the LED 13a is formed of LEDs each emitting white light, but for example, an ultraviolet light source, a blue light source, or a green light source may also be adopted. Furthermore, there may be a mode in which light sources can independently emit different colors of light by providing the light sources that respectively emit different colors of light. Thus, different images can be obtained by obtaining captured images by illumination with different colors of light, and examination and diagnosis on a skin lesion site can be easily performed by comparing the different images and superimposing the images. Furthermore, in the embodiment, the LEDs 13a serving as light sources are supported by the LED substrate 13 by being mounted on the LED substrate 13, but as far as a light source is connected to a power source thereof via the substrate, the light source is not necessarily supported by the substrate and may be supported by another suitable member.

Moreover, in the embodiment, the heatsink 70 having a plate-like shape is used as the heat dissipation member in the present invention, but a member having another suitable shape may also be used. Additionally, in the embodiment, the heatsink 70 serving as the heat dissipation member is mounted (installed) on the LED substrate 13, but as far as the heat dissipation member can dissipate (transmit) heat of the light source to the cover member, the heat dissipation member may also be installed in an appropriate member such as a light source.

Furthermore, in the above-described case, the cover member 24 is set close to or inserted into the oral cavity during intraoral photographing. However, as far as light having sufficient illuminance can be emitted, a lesion site inside the oral cavity can be photographed from the outside of the oral cavity without inserting the cover member 24 into the oral cavity. In this case, cleaning work after photographing becomes unnecessary, and an examination time can be shortened.

Furthermore, the imaging device according to the present embodiment is not limited to the imaging device for intraoral photographing like the camera 1 described in the above embodiment. Also, a subject is not limited to a lesion site inside the oral cavity. For example, the present invention can also be applied to an imaging device or the like to photograph the inside of a hole illuminated with light while the light is emitted to the inside of the hole formed in a structure or the like having a low temperature or low humidity.

Additionally, in the above-described camera 1, described is the case where the camera body 10 is provided with the shutter button 18 and the touch panel screen (not illustrated) in order to execute various kinds of settings for the camera 1. However, operation receiving units such as the shutter button 18 and the touch panel screen (not illustrated) may be provided in an operation unit physically separated from the camera body 10. The camera body 10 and the operation unit can bidirectionally communicate by using an existing communication technology. A photographer can perform various kinds of settings for the camera body 10, shutter operation, and the like by operating the operation unit. Additionally, in the embodiment, an optical unit is a type applied to the camera 1, but not limited thereto, for example, the optical unit may be a type by which a user observes a target via a cover member in a state where the target is illuminated by a light source without having a structure such as an imaging element for photographing. In this case, the optical unit may not necessarily include a lens.

What is claimed is:

1. An imaging device comprising:
   a cover body having an opening in a distal end thereof, wherein a distal portion of the cover body is configured to be inserted into an oral cavity of a patient;
   an imaging lens system;
   a transparent outer cover of the imaging lens system, wherein the transparent outer cover covers the opening in the distal end of the cover body;
   a substrate arranged inside the cover body;
   a light source mounted on the substrate and provided in the distal portion of the cover body, the light source being configured to emit light distally in a light emitting direction to outside of the imaging device, through the transparent outer cover, to illuminate a target; and
   a heat sink including a seat portion having an annular shape with a through-hole, and a protruding portion that protrudes distally from the seat portion,
   wherein:
   the seat portion of the heat sink contacts the substrate,
   the imaging lens system extends through the through-hole in the annular shape of the seat portion of the heat sink,
   the protruding portion of the heat sink protrudes distally from the seat portion in the light emitting direction towards the transparent outer cover,
   a distal end of the protruding portion of the heat sink is positioned between the transparent outer cover and the light source, along the light emitting direction, and
   the substrate and the heat sink are configured to dissipate heat of the light source to the transparent outer cover.

2. The imaging device according to claim 1, wherein the light source is one of a plurality of light sources that are mounted on the substrate, the protruding portion is one of a plurality of protruding portions that protrude from the seat portion of the heat sink, and
   wherein the protruding portions and the light sources are provided to correspond to each other on a one-to-one basis.

3. The imaging device according to claim 1, further comprising a filter provided inside the cover body and configured to transmit the light emitted from the light source to the transparent outer cover,
   wherein:
   the filter contacts the protruding portion of the heat sink,
   the filter surrounds part of the imaging lens system, and
   the heat of the light source is dissipated to the transparent outer cover via the substrate, the seat portion, the protruding portion, the filter, and a space between the filter and the transparent outer cover.

4. The imaging device according to claim 1, wherein the cover body has a truncated cone shape with a hollow interior, such that the cover body tapers from a first side thereof to a second side thereof,
   wherein the opening is provided in the second side of the cover body.

5. The imaging device according to claim 4, wherein the substrate, the light source, and the heat sink are all provided within the hollow interior of the truncated cone shape of the hollow body.

6. An optical unit comprising:
   a cover body having an opening in a distal end thereof, wherein a distal portion of the cover body is configured to be inserted into an oral cavity of a patient;
   a transparent outer cover which is configured to transmit light, wherein the transparent outer cover covers the opening in the distal end of the cover body;
   a substrate arranged inside the cover body;
   a light source mounted on the substrate and provided in the distal portion of the cover body, the light source being configured to emit light distally in a light emitting direction to outside of the optical unit, through the transparent outer cover, to illuminate a target; and
   a heat sink including a seat portion having an annular shape with a through-hole, and a protruding portion that protrudes distally from the seat portion,
   wherein:
   the seat portion of the heat sink contacts the substrate,
   the protruding portion of the heat sink protrudes distally from the seat portion in the light emitting direction towards the transparent outer cover,
   a distal end of the protruding portion of the heat sink is positioned between the transparent outer cover and the light source, along the light emitting direction, and
   the substrate and the heat sink are configured to dissipate heat of the light source to the transparent outer cover.

7. The optical unit according to claim 6, wherein the light source is one of a plurality of light sources that are mounted on the substrate, the protruding portion is one of a plurality of protruding portions that protrude from the seat portion of the heat sink, and
   wherein the protruding portions and the light sources are provided to correspond to each other on a one-to-one basis.

8. The optical unit according to claim 6, further comprising a filter provided inside the cover body and configured to transmit the light emitted from the light source to the transparent outer cover,
   wherein:
   the filter contacts the protruding portion of the heat sink,
   the filter surrounds part of the imaging lens system, and
   the heat of the light source is dissipated to the transparent outer cover via the substrate, the seat portion, the protruding portion, the filter, and a space between the filter and the transparent outer cover.

9. The optical unit according to claim 6, wherein the cover body has a truncated cone shape with a hollow interior, such that the cover body tapers from a first side thereof to a second side thereof,
   wherein the opening is provided in the second side of the cover body.

10. The optical unit according to claim 9, wherein the substrate, the light source, and the heat sink are all provided within the hollow interior of the truncated cone shape of the hollow body.

\* \* \* \* \*